(12) United States Patent
Twede et al.

(10) Patent No.: US 9,478,692 B1
(45) Date of Patent: *Oct. 25, 2016

(54) X-RAY MULTIBAND EMISSION AND CONVERSION

(71) Applicant: Lockheed Martin Corporation, Bethesda, MD (US)

(72) Inventors: David R. Twede, Orlando, FL (US); Del E. Vicker, Orlando, FL (US)

(73) Assignee: Lackheed Martin Corporation, Bethesda, MD (US)

( * ) Notice: Subject to any disclaimer, the term of this patent is extended or adjusted under 35 U.S.C. 154(b) by 105 days.

This patent is subject to a terminal disclaimer.

(21) Appl. No.: 14/095,513

(22) Filed: Dec. 3, 2013

Related U.S. Application Data

(63) Continuation-in-part of application No. 13/891,692, filed on May 10, 2013.

(60) Provisional application No. 61/645,514, filed on May 10, 2012.

(51) Int. Cl.
*H01L 27/146* (2006.01)
*H01L 31/12* (2006.01)
(Continued)

(52) U.S. Cl.
CPC ........... *H01L 31/125* (2013.01); *A61B 6/4241* (2013.01); *B82Y 20/00* (2013.01);
(Continued)

(58) Field of Classification Search
CPC ...... G01N 23/00; G01N 23/02; G01N 23/04; G01N 23/06; G01N 23/08; G01N 23/083; G01N 23/087; G01N 2223/206; G01N 2223/30; G01N 2223/40; G01N 2223/423; G01N 23/18; G21K 4/00; G21K 4/02; G21K 4/04; G21K 4/06; G21K 4/08; G21K 4/10; G21K 4/12; H01J 31/50; H01J 31/56; H01J 29/08; H01J 29/18; H01J 29/20; A61B 6/42; A61B 6/4208; A61B 6/4241; H01L 27/00; H01L 27/14; H01L 27/142; H01L 27/144; H01L 27/146; H01L 27/14601; H01L 27/14663; H01L 27/14676; H01L 31/0232; H01L 31/02322; H01L 31/125; B82Y 20/00; B82Y 30/00; B82Y 40/00; B82Y 99/00; G01T 1/00; G01T 1/16; G01T 1/1612; G01T 1/1617; G01T 1/164; G01T 1/20; G01T 1/2002; G01T 1/2006; G01T 1/2018; G01T 1/36; G01T 1/362; G01T 7/00; G01T 7/12; C09K 11/00; C09K 11/02; C09K 11/06; C09K 11/08; C01P 2004/64; G02B 1/00; G02B 1/002; G02B 1/005; G02B 1/02; G02B 6/00; G02B 6/10; G02B 6/102; G02B 6/293; G02B 6/42; G02B 6/4295; G02B 6/4296; G02B 6/4298; G02B 6/43; G02B 26/08; G02B 2207/101
USPC ....... 378/5, 16, 51, 53, 57, 62, 91, 98, 98.8, 378/98.9, 98.11, 98.12, 189, 204, 210; 250/370.01, 370.06, 370.08, 370.09, 250/370.11, 370.12
See application file for complete search history.

(56) References Cited

U.S. PATENT DOCUMENTS 4,872,187 A * 10/1989 Nakahata ............. G01N 23/046 378/17
6,292,534 B1 * 9/2001 Linders ................ A61B 6/4233 348/E5.086

(Continued)

FOREIGN PATENT DOCUMENTS

WO 2012174173 A2 12/2012

OTHER PUBLICATIONS

Ferrer, Domingo et al., "Atomic structure of three-layer Au/Pd nanoparticles revealed by aberration-corrected scanning transmission electron microscopy," Journal of Materials Chemistry, vol. 18, Mar. 19, 2008, RSCPublishing, 6 pages.
(Continued)

*Primary Examiner* — Anastasia Midkiff
(74) *Attorney, Agent, or Firm* — Withrow & Terranova, PLLC

(57) ABSTRACT

A photonic conversion layer receives incoming photons in a plurality of X-ray bands, the incoming photons passing through an item on a path from an X-ray source to the photonic conversion layer. The incoming photons are converted in each X-ray band of the plurality of X-ray bands to outgoing photons in corresponding different converted bands in the visible-to-near infrared (VNIR) spectrum. The outgoing photons are emitted in the corresponding different converted bands in the VNIR spectrum. A sensor detects the outgoing photons in the corresponding different converted bands in the VNIR spectrum and generates output data representative of the outgoing photons. Image data is generated based on the output data.

21 Claims, 11 Drawing Sheets

(51) Int. Cl.
| | |
|---|---|
| G01N 23/087 | (2006.01) |
| B82Y 20/00 | (2011.01) |
| G01T 1/20 | (2006.01) |
| C09K 11/00 | (2006.01) |
| H01L 31/0232 | (2014.01) |
| A61B 6/00 | (2006.01) |
| G01T 1/36 | (2006.01) |
| G02B 6/42 | (2006.01) |

(52) U.S. Cl.
CPC ............ *G01T 1/2002* (2013.01); *G01T 1/362* (2013.01); *H01L 27/14663* (2013.01); *H01L 31/02322* (2013.01); *C01P 2004/64* (2013.01); *C09K 11/00* (2013.01); *G01N 23/087* (2013.01); *G01T 1/2006* (2013.01); *G01T 1/2018* (2013.01); *G02B 6/4298* (2013.01); *G02B 2207/101* (2013.01); *H01L 27/14601* (2013.01); *H01L 27/14676* (2013.01)

(56) References Cited

U.S. PATENT DOCUMENTS

| | | | |
|---|---|---|---|
| 6,950,492 B2 | 9/2005 | Besson | |
| 6,960,767 B1 | 11/2005 | Do et al. | |
| 7,121,474 B2 | 10/2006 | Bourianoff et al. | |
| 7,532,703 B2* | 5/2009 | Du | A61B 6/032 378/116 |
| 7,804,103 B1 | 9/2010 | Zhai et al. | |
| 7,937,280 B1 | 5/2011 | Leung et al. | |
| 7,972,557 B2 | 7/2011 | Hyde et al. | |
| 8,536,532 B1 | 9/2013 | Kross et al. | |
| 9,105,273 B1 | 8/2015 | Twede et al. | |
| 9,110,292 B1 | 8/2015 | Twede et al. | |
| 9,157,872 B1 | 10/2015 | Twede | |
| 2002/0117635 A1 | 8/2002 | Shinada et al. | |
| 2002/0149692 A1 | 10/2002 | Tomita et al. | |
| 2005/0025280 A1* | 2/2005 | Schulte | G01N 23/04 378/57 |
| 2005/0084064 A1* | 4/2005 | McIntyre | G01N 23/04 378/54 |
| 2005/0111017 A1* | 5/2005 | Takahashi | H04N 1/6027 358/1.9 |
| 2006/0054863 A1* | 3/2006 | Dai | B82Y 10/00 252/301.4 R |
| 2007/0044559 A1* | 3/2007 | Andrews | G01N 29/4427 73/584 |
| 2009/0003514 A1* | 1/2009 | Edic | G01V 5/005 378/10 |
| 2009/0027518 A1 | 1/2009 | Kita | |
| 2009/0059406 A1 | 3/2009 | Powers et al. | |
| 2010/0142062 A1 | 6/2010 | Asami et al. | |
| 2010/0261263 A1* | 10/2010 | Vo-Dinh | B82Y 30/00 435/287.1 |
| 2011/0021970 A1 | 1/2011 | Vo-Dinh et al. | |
| 2011/0129537 A1* | 6/2011 | Vo-Dinh | A61K 41/0066 424/490 |
| 2011/0181191 A1 | 7/2011 | Smith et al. | |
| 2011/0222658 A1* | 9/2011 | Radley | G01V 5/0016 378/62 |
| 2012/0027175 A1* | 2/2012 | Radley | G01V 5/0016 378/82 |
| 2013/0051529 A1* | 2/2013 | Basu | G01N 23/087 378/64 |
| 2013/0215912 A1 | 8/2013 | Shkunov et al. | |
| 2013/0327928 A1 | 12/2013 | Leach et al. | |
| 2014/0194314 A1 | 7/2014 | Walsworth et al. | |
| 2015/0083923 A1* | 3/2015 | Stanton | G01T 1/20 250/367 |

OTHER PUBLICATIONS

Non-Final Office Action for U.S. Appl. No. 14/169,906 mailed Sep. 18, 2014, 16 pages.
Non-Final Office Action for U.S. Appl. No. 13/891,692, mailed Apr. 16, 2015, 10 pages.
Notice of Allowance for U.S. Appl. No. 14/107,231, mailed Apr. 16, 2015, 9 pages.
Notice of Allowance for U.S. Appl. No. 14/169,906, mailed Apr. 6, 2015, 8 pages.
Notice of Allowance for U.S. Appl. No. 14/210,809, mailed Jun. 9, 2015, 7 pages.
Author Unknown, "Luminescent Up-conversion Nanocrystals," Biochemical Products, Sigma-Aldrich Co. LLC, 2013, http://www.sigmaaldrich.com/life-science/biochemicals/biochemical-products, accessed Apr. 23, 2013, 1 page.
Author Unknown, "Sunstone Upconverting Nanocrystals UCP 475," Material Safety Data Sheet, Version 5.1, Sigma-Aldrich Co. LLC, Revised May 31, 2012, 6 pages.
Author Unknown, "Sunstone Luminescent UCP Nanocrystals," Technical Document, Sigma-Aldrich Co. LLC, http://www.sigmaaldrich.com/technical-documents/articles/biology/upconverting-ucp-nanocrystals.html, accessed Apr. 23, 2013, 6 pages.
Shun, Poh Hou, "Towards a High Quality Polarization-Entangled Multi-Photon Source," A Thesis Submitted for the Degree of Master of Science, Department of Physics, National University of Singapore, 2009, 113 pages.
Gorris et al., "Photon-upconverting nanoparticles for optical encoding and multiplexing of cells, biomolecules, and microspheres," Angewandte Chemie International Edition, vol. 52, No. 13, Mar. 25, 2013, pp. 3584-3600 (abstract only).
McCutcheon et al., "Broadband frequency conversion and shaping of single photons emitted from a nonlinear cavity," Optics Express, vol. 17, No. 25, Dec. 7, 2009, 15 pages.
Suyver et al., "Novel materials doped with trivalent lanthanides and transition metal ions showing near-infrared to visible photon upconversion," Optical Materials, vol. 27, No. 6, Mar. 2005, pp. 1111-1130 (abstract only).
Tyson, Jeff et al., "How Airport Security Works," the Pallet, vol. 55, Feb. 2008, travel.howstuffworks.com/airport-security.htm, 5 pages.
Girard, C. et al., "The physics of the near-field," Reports on Progress in Physics, vol. 63, No. 6, Jun. 2000, IOP Publishing Ltd., 46 pages.
Jain, P., "Plasmons in Assembled Metal Nanostructures: Radiative and Nonradiative Properties, Near-Field Coupling and its Universal Scaling Behavior," Doctoral Dissertation, Georgia Institute of Technology, Apr. 2008, 316 pages.
Pucci, A. et al., "Chapter 8: Electromagnetic Nanowire Resonances for Field-Enhanced Spectroscopy," Lecture Notes in Nanoscale Science and Technology, vol. 3: One-Dimensional Nanostructures, Springer Science+Business Media, LLC, 2008, pp. 175-215.
Tiwari, S. et al., "A silicon nanocrystals based memory," Applied Physics Letters, vol. 68, No. 10, Mar. 4, 1996, American Institute of Physics, 3 pages.
Final Office Action for U.S. Appl. No. 13/891,692, mailed Sep. 18, 2015, 11 pages.
Non-Final Office Action for U.S. Appl. No. 14/100,497, mailed Sep. 24, 2015, 9 pages.
Ye, Xingchen, et al., "Competition of shape and interaction patchiness for self-assembling nanoplates," Nature Chemistry: Advance Online Publication, vol. 5, Issue 6, Paper No. NCHEM-12070903B, May 12, 2013, Nature, www.nature.com/naturechemistry, 9 pages.
Non-Final Office Action for U.S. Appl. No. 13/891,692, mailed Jan. 7, 2016, 10 pages.
Final Office Action for U.S. Appl. No. 13/891,692, mailed Jun. 13, 2016, 7 pages.
Notice of Allowance and Applicant-Initiated Interview Summary for U.S. Appl. No. 14/100,497, mailed Apr. 29, 2016, 10 pages.
Non-Final Office Action for U.S. Appl. No. 14/880,612, mailed Apr. 21, 2016, 18 pages.
Notice of Allowance and AFCP 2.0 Decision for U.S. Appl. No. 13/891,692, mailed Aug. 4, 2016, 12 pages.

* cited by examiner

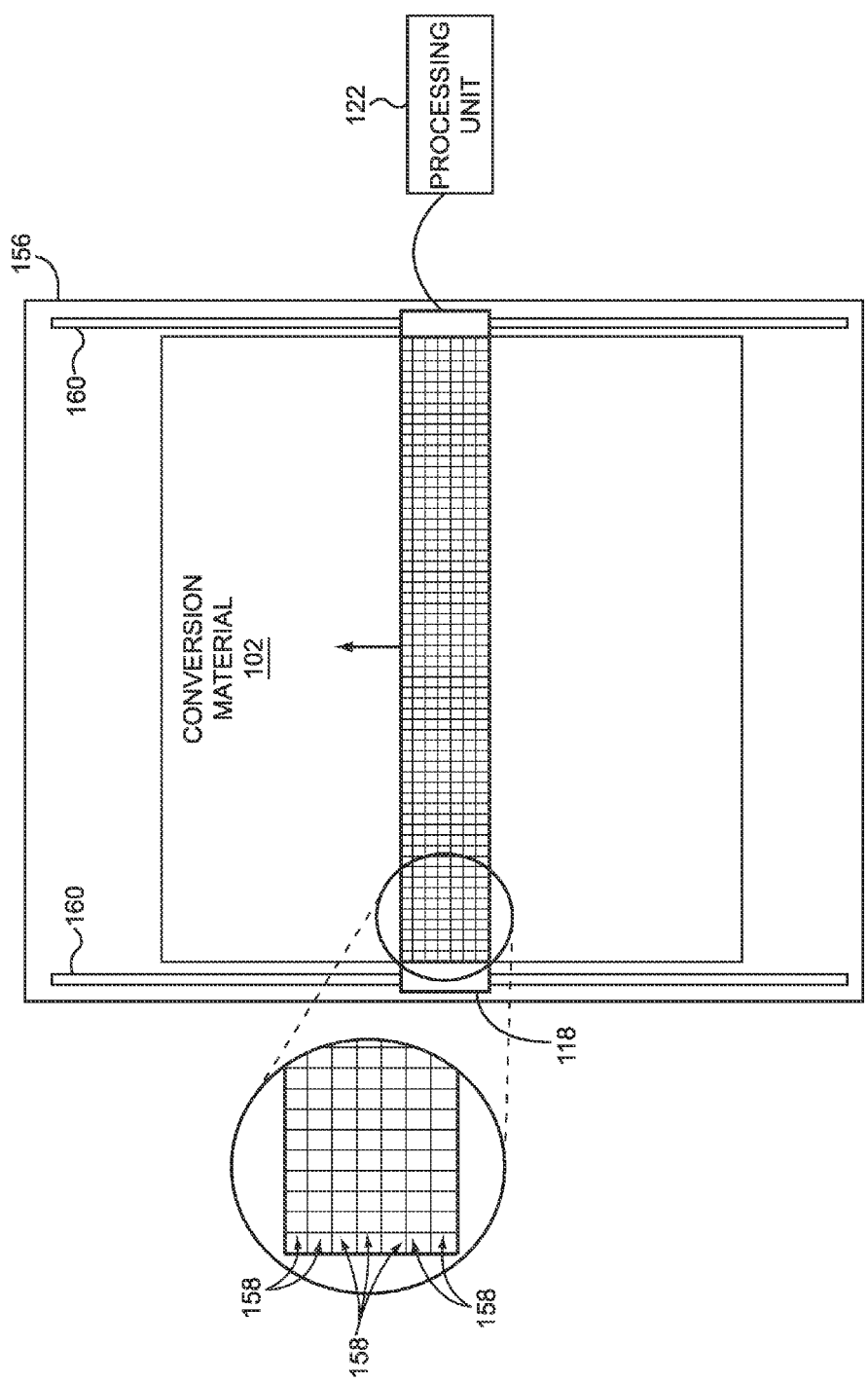

X-RAY MULTIBAND EMISSION AND CONVERSION

RELATED APPLICATIONS

This application is a continuation-in-part of and claims priority to co-pending patent application Ser. No. 13/891,692, filed May 10, 2013, entitled "MULTI-SPECTRAL PHOTON CONVERTING IMAGING APPARATUS," which claims the benefit of provisional patent application Ser. No. 61/645,514, filed May 10, 2012, entitled "PHOTON CONVERSION IMAGING USING DOPED NANOPARTICLE MATERIALS," the disclosures of which are hereby incorporated herein by reference in their entireties.

TECHNICAL FIELD

The embodiments generally relate to X-ray imaging, and in particular to the emission and conversion of multiple bands of X-ray energy to corresponding converted bands of energy for imaging purposes.

BACKGROUND

Electromagnetic radiation in the X-ray wavelengths ("X-ray energy") is relatively energetic and can be useful in a variety of applications where penetration of materials is desired, including the generation of images of bones and other materials in a human body. The ability to detect X-ray energy requires relatively specialized photo-detectors, and such specialized photo-detectors render X-ray energy detection relatively expensive, and consequently impractical in a number of applications for which X-ray energy may otherwise be useful. Image sensors capable of detecting electromagnetic radiation in the visible to near-infrared (VNIR) bands, on the other hand, are relatively inexpensive. Accordingly, the ability to depict X-ray energy in the VNIR bands would allow the use of lower-cost sensors, and facilitate the use of X-ray energy in relatively low-cost applications.

SUMMARY

The embodiments relate to the emission and conversion of multiple bands of X-ray energy to corresponding bands of energy in other wavelengths, the detection of the corresponding bands of energy, and the generation of an image based on the detected energy. In one embodiment, a method of generating image data is provided. A photonic conversion layer receives incoming photons in a plurality of X-ray bands. The incoming photons pass through an item on a path from an X-ray source to the photonic conversion layer. The photonic conversion layer converts the incoming photons in each X-ray band to outgoing photons in corresponding different converted bands in the visible-to-near infrared (VNIR) spectrum. The photonic conversion layer emits the outgoing photons in the corresponding different converted bands in the VNIR spectrum. A sensor detects the outgoing photons in the corresponding different converted bands in the VNIR spectrum and generates output data representative of the outgoing photons. A processor generates image data based on the output data.

The present embodiments have applicability in a wide variety of applications where determining the composition of materials is useful, including, for example, medicine, security, manufacturing, and the like.

In one embodiment, the X-ray source is configured to receive a selection of a particular energy scheme of a plurality of energy schemes. Based on the selection, the X-ray source emits the incoming photons in a plurality of X-ray bands in accordance with the particular energy scheme. Thus, depending on the application, an operator may select a particular energy scheme that involves X-rays of desired bands useful for that particular application.

In one embodiment, the incoming photons are emitted by the X-ray source in a known pattern that is identified in a reference profile. The processor generates the image data based on the output data from the sensor, and on the reference profile. In one embodiment, the processor receives an energy scheme identifier that identifies the particular energy scheme used by the X-ray source to generate the incoming photons. Based on the energy scheme identifier, the processor accesses the corresponding reference profile from a plurality of different reference profiles. Each reference profile may identify, for example, a spectral distribution and intensity emitted by the photonic conversion layer upon receiving incoming photons transmitted by the X-ray source in accordance with the corresponding energy scheme without any item in the path between the X-ray source and the photonic conversion layer.

In one embodiment, the processor determines an absorption signature of the item based on the output data and, based on the absorption signature, identifies a component of the item. For example, where the item is a living organism, the component may comprise a biological component, such as a composition of a tumor or other mass. In a security context, the component may comprise a chemical or other substance that has been identified as being hazardous.

In another embodiment, a system is provided. The system includes a photonic conversion layer that is configured to receive incoming photons in a plurality of X-ray bands. The incoming photons pass through an item on a path from an X-ray source to the photonic conversion layer. The photonic conversion layer is further configured to convert the incoming photons in each X-ray band of the plurality of X-ray bands to outgoing photons in corresponding different converted bands in the VNIR spectrum, and to emit the outgoing photons in the corresponding different converted bands in the VNIR spectrum. The system further includes a sensor that is configured to detect the outgoing photons in the corresponding different converted bands in the VNIR spectrum and generate output data representative of the outgoing photons. The system also includes a processor configured to generate image data based on the output data.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 11 is a block diagram of a sensor according to another embodiment.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The embodiments relate to the conversion of photons in received bands to photons in converted bands, and the detection and imaging thereof. Among other advantages, some embodiments facilitate the use of relatively low cost, widely available image sensors to generate images based on photons in received bands that such image sensors would not be capable of detecting. Some embodiments relate to the emission and conversion of multiple bands of X-ray energy to corresponding bands of energy in other wavelengths, detection of such energy, and the generation of an image based on the detected energy.

Figure 1:
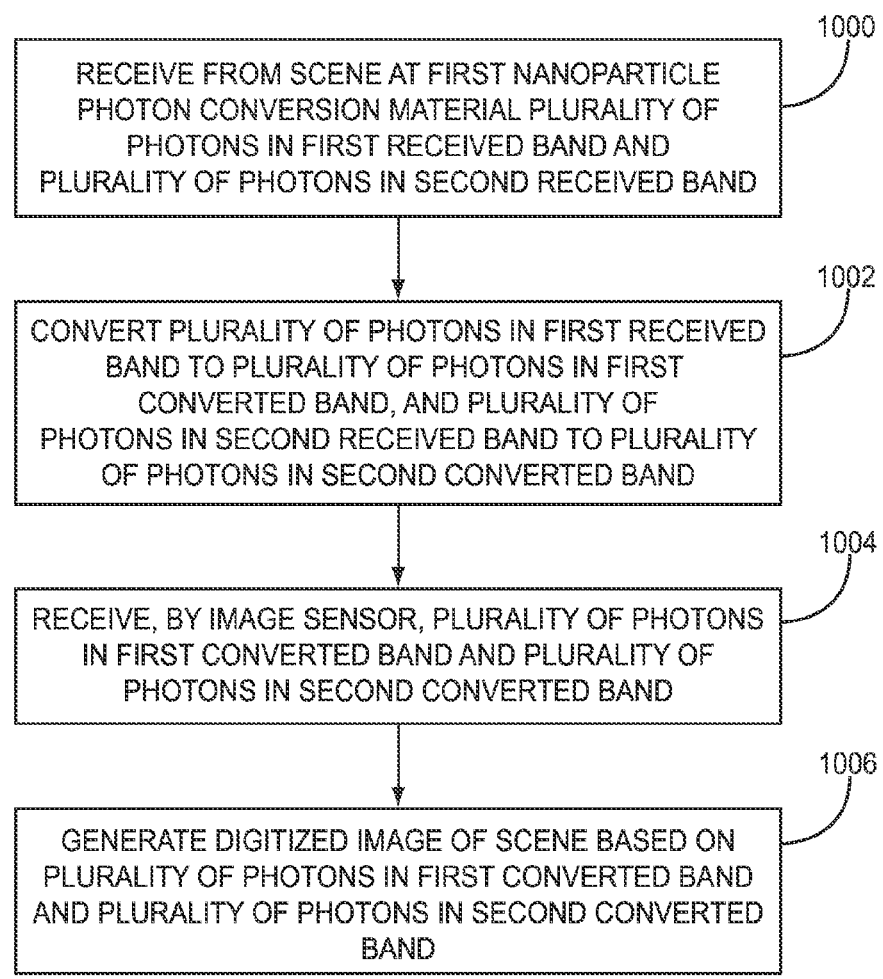
FIG. 1 is a flowchart of a process for generating an image according to one embodiment.

FIG. 1 is a flowchart of a process for generating an image according to one embodiment. A nanoparticle (NP) photon conversion material receives from a scene a plurality of photons in a first received band and a plurality of photons in a second received band (block 1000). The use herein of ordinals, such as first, second, or third, in conjunction with an element is solely for distinguishing what might otherwise be similar or identical labels, such as "first band" and "second band," and does not imply a priority, a type, an importance, or other attribute, unless otherwise stated herein. The phrase "band" refers to a range of photon wavelengths.

The NP photon conversion material converts the plurality of photons in the first received band to a plurality of photons in a first converted band, and the plurality of photons in the second received band to a plurality of photons in a second converted band (block 1002). The number of photons in the first received band may differ from the number of photons in the first converted band. An image sensor receives the plurality of photons in the first converted band and the plurality of photons in the second converted band (block 1004). The image sensor generates a digitized image of the scene based on the plurality of photons in the first converted band and the plurality of photons in the second converted band (block 1006). For purposes of illustration, many of the embodiments will be discussed in the context of received bands comprising non-visible bands, and converted bands comprising visible and/or near-infrared bands, but the embodiments are not limited to converted bands of any particular wavelengths. However, the conversion of photons to visible and/or near-infrared bands, in some embodiments, may facilitate the use of relatively low-cost image sensors used widely in digital cameras since such low-cost image sensors are typically sensitive in the visible and near-infrared bands.

Figure 2:
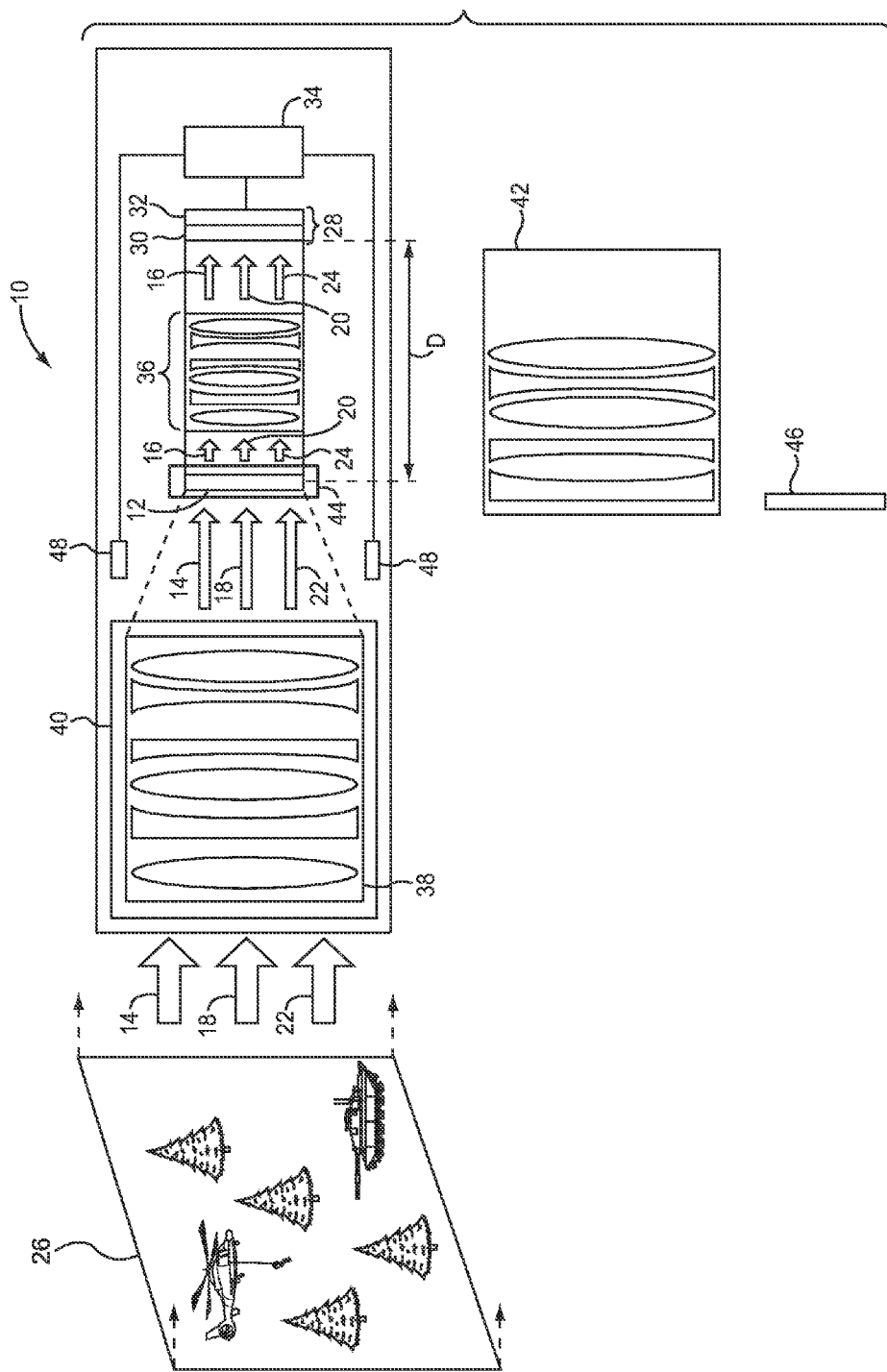
FIG. 2 is a block diagram of a multi-spectral imaging apparatus according to one embodiment.

FIG. 2 is a block diagram of a multi-spectral imaging apparatus 10 according to one embodiment. The imaging apparatus 10 includes a first NP photon conversion material 12 that is configured to convert one or more pluralities of photons in received bands to corresponding pluralities of photons in converted bands. For purposes of illustration, the embodiments will be discussed herein in the context of three received bands and three converted bands, but the embodiments are not limited to any number of received bands or converted bands. Generally, the number of bands utilized will be system dependent, and in large part may be dependent on the particular image sensor used, as discussed in greater detail herein.

In this example, the first NP photon conversion material 12 is configured to convert a plurality of photons 14 in a first received band to a plurality of photons 16 in a first converted band, a plurality of photons 18 in a second received band to a plurality of photons 20 in a second converted band, and a plurality of photons 22 in a third received band to a plurality of photons 24 in a third converted band. The plurality of photons 14 in the first received band, the plurality of photons 18 in the second received band and the plurality of photons 22 in the third received band are received from a scene 26, which may comprise, for example, all objects and matter that falls within the field of view (FOV) of the imaging apparatus 10, or the FOV of a device to which the imaging apparatus 10 is communicatively coupled.

The first NP photon conversion material 12 comprises materials, such as frequency converting nanocrystals, that are capable of "upconverting" photons of one energy level to photons of a higher energy level, such as upconverting photons in an infrared band to photons in a visible band or other converted band, or "downconverting" photons of one energy level to photons of a lower energy level, such as downconverting photons in an X-ray band to photons in a visible band or other converted band. In one embodiment, the first NP photon conversion material 12 may be coated onto a glass, or other transmissive substrate, that is transparent to photons in the converted bands, according to the particular upconverting or downconverting scheme used.

Generally such materials are engineered to absorb energy at one wavelength and emit energy at a different wavelength, thus "converting" photons of one band to photons of another band. Such materials may be synthesized, for example, using specific compositions of individual rare earth elements and other host elements. Upconversion may occur through a combination of a trivalent rare-earth sensitizer (e.g., Ytterbium (Yb), Neodymium (Nd), Erbium (Er), or Samarium (Sm)) as the element that initially absorbs the electromagnetic radiation and a second lanthanide activator ion (e.g., Erbium (Er), Holmium (Ho), Praseodymium (Pr), Thulium (Tm)) in an optical passive crystal lattice that serves as the emitting elements. By varying the concentrations and ratios of rare earth elements, different emission spectra can be elicited from the same combination of elements. Such materials are available, for example, from Sigma-Aldrich, 3050 Spruce Street, St. Louis, Mo. 63103. In some embodiments, the first NP photon conversion material 12 may comprise a mixture of elements that performs the desired conversion of received bands to converted bands, or alternatively, the first NP photon conversion material 12 may be patterned in a desired configuration, such as a striped configuration, a checkerboard configuration, or may be configured as grating planes, or as a linear variable filter.

The imaging apparatus 10 also includes an image sensor 28 that is configured to receive the plurality of photons 16 in the first converted band, the plurality of photons 20 in the second converted band, and the plurality of photons 24 in the third converted band, and based thereon, generate a digital image. The image sensor 28 comprises a photodetector array 30 and readout circuitry 32. Some of the functionality discussed herein with regard to the imaging apparatus 10 may be implemented under the control of a controller 34. The controller 34 may comprise a programmable central processing unit (CPU), application specific integrated circuit, or the like, that is configured to implement functionality discussed herein. In one embodiment, programming instructions may be stored on a memory (not illustrated), and executed by the controller 34 to implement functionality described herein.

The photodetector array 30 is multi-spectral and capable of detecting photons at different bands, and in particular capable of detecting photons at the different converted bands that are received by the photodetector array 30. In one embodiment, the photodetector array 30 includes a color-filter array capable of separating different incoming visible and/or near-infrared converted bands.

In the embodiment illustrated in FIG. 2, the first NP photon conversion material 12 may be positioned at a distance D from the image sensor 28. The distance D may position the first NP photon conversion material 12 in an image plane that is conjugant to an image plane of the photodetector array 30. While the distance D is system dependent, the distance D, in some embodiments, may range from 1 mm to 100 mm. The imaging apparatus 10 may include a lens arrangement 36 that is configured to direct the plurality of photons 16 in the first converted band, the plurality of photons 20 in the second converted band, and the plurality of photons 24 in the third converted band onto the image sensor 28.

The imaging apparatus 10 may also include a lens arrangement 38 that is configured to direct the plurality of photons 14 in the first received band, the plurality of photons 18 in the second received band and the plurality of photons 22 in the third received band onto the first NP photon conversion material 12. The lens arrangement 38 may be configured to direct photons in particular received bands, but be incapable of, or less efficient at, directing photons of other received bands. Accordingly, in one embodiment, the imaging apparatus 10 includes a lens arrangement receiver 40 that has a released mode and an engaged mode. The lens arrangement receiver 40 is configured to fix the lens arrangement 38 with respect to the first NP photon conversion material 12 when in the engaged mode. In the released mode, a user may remove the lens arrangement 38 from the lens arrangement receiver 40, and insert a different lens arrangement 42 that may be configured to direct photons in one or more different received bands onto the first NP photon conversion material 12. The lens arrangement receiver 40 may comprise any suitable interface, such as a threaded interface, friction interface, or the like.

Similarly, the first NP photon conversion material 12 may be configured to convert pluralities of photons of particular received bands into corresponding pluralities of photons of converted bands, but be ineffective at converting photons of other received bands. Accordingly, the imaging apparatus 10 may include a NP photon conversion material receiver 44 that has a released mode and an engaged mode, and that is configured to fix the NP photon conversion material 12 with respect to the image sensor 28 when in the engaged mode. If the detection of different pluralities of received bands are of interest to a user, the user may release the first NP photon conversion material 12 from the NP photon conversion material receiver 44, and insert a second NP photon conversion material 46 into the NP photon conversion material receiver 44. Thus, the imaging apparatus 10 may facilitate the conversion of any desired pluralities of photons of received bands to desired pluralities of photons of converted bands through the selection of a particular NP photon conversion material, and inserting particular NP photon conversion material into the NP photon conversion material receiver 44.

For example, the first NP photon conversion material 12 may convert a plurality of photons in the short-wave infrared band to a plurality of photons in a red visible band, and a plurality of photons in the mid-wave infrared band to a plurality of photons in a blue visible band. The second NP photon conversion material 46 may convert a plurality of photons in a particular long-wave infrared band to a plurality of photons in a red visible band, and a plurality of photons in a different long-wave infrared band to a plurality of photons in a blue visible band.

The use of different NP photon conversion materials may be done independent of, or in conjunction with, the use of a particular lens arrangement 38, 42, and insertion thereof into the lens arrangement receiver 40. For example, the lens arrangement 38 may be configured to direct photons in the short-wave and mid-wave infrared bands. The lens arrangement 42 may be configured to direct photons in the long-wave band. Different NP photon conversion materials and/or lens arrangements may be used to generate images of the same scene 26.

The imaging apparatus 10 may include one or more energy sources 48 that are configured to increase an energy level of the first NP photon conversion material 12. Increasing the energy level of the first NP photon conversion material 12 may increase photon conversion efficiency. The energy sources 48 may emit energy at a particular wavelength that when absorbed by the first NP photon conversion material 12 increases the energy level of the first NP photon conversion material 12. In one embodiment, during a down-cycle, sometimes referred to as an off-cycle, of the image sensor 28, the controller 34 may activate the energy sources 48 to emit energy at the desired wavelength(s) for a period of time during the off-cycle. The controller 34 may then, immediately prior to an up-cycle, sometimes referred to as an on-cycle, of the image sensor 28, deactivate the energy sources 48. In other embodiments, particularly wherein the energy sources 48 comprise an electromagnetic field, or an electron beam, the energy sources 48 may remain continuously on during off- and on-cycles of the image sensor 28. In some embodiments, the energy sources 48 may comprise an electromagnetic energy source, such as a laser light, or an electric energy source, such as a static field generated from a transparent capacitor plate positioned on either side of the first NP photon conversion material 12.

Figure 3:
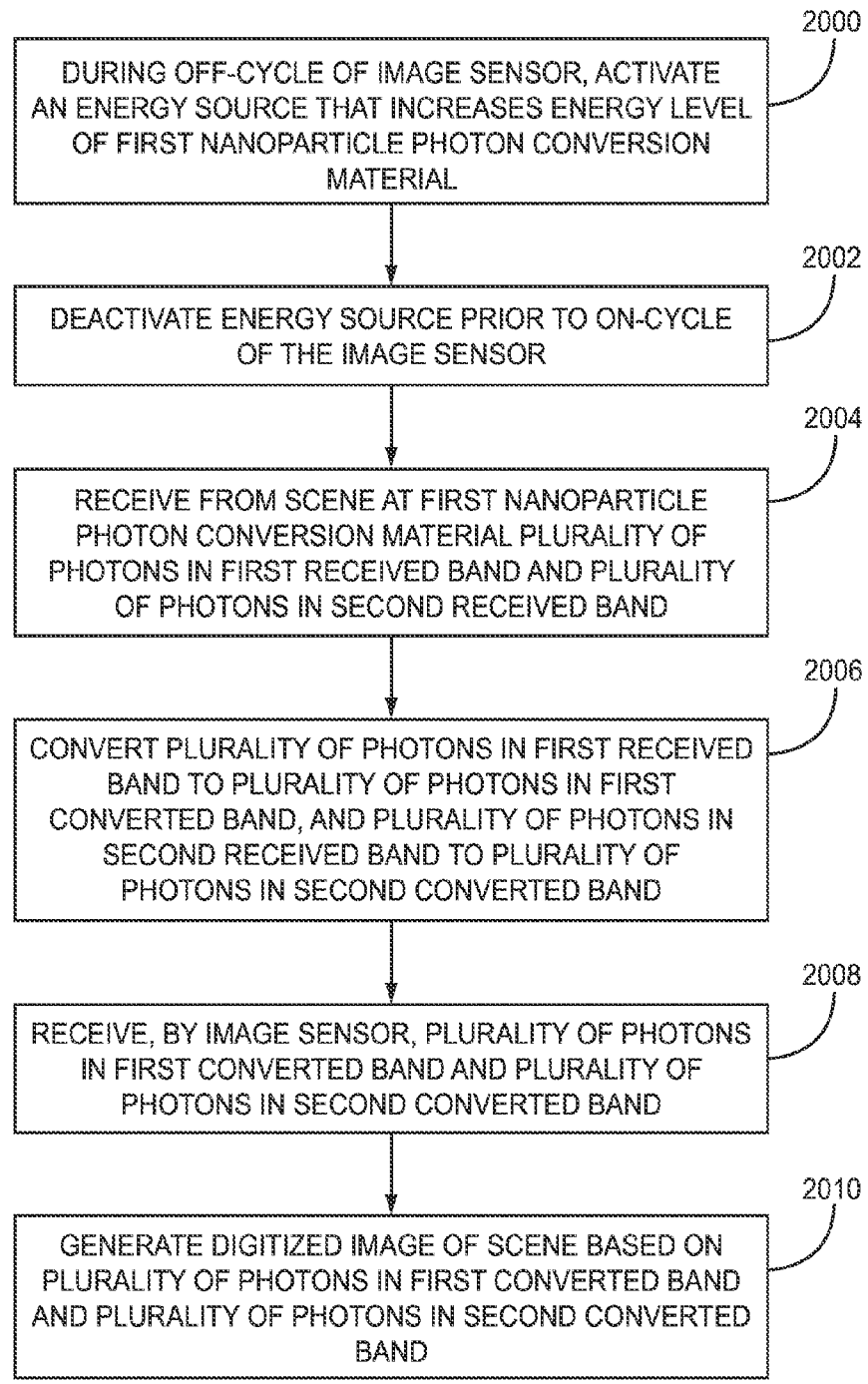
FIG. 3 is a flowchart of a method for increasing an energy level of a nanoparticle photon conversion material according to one embodiment.

FIG. 3 is a flowchart of a method for increasing an energy level of a NP photon conversion material according to one embodiment, and will be discussed in conjunction with FIG. 2. During an off-cycle of the image sensor 28, the controller 34 activates the energy sources 48 to increase the energy level of the first NP photon conversion material 12 (block 2000). Prior to the on-cycle of the image sensor 28, the controller 34 deactivates the energy sources 48 (block 2002). Processing in blocks 2004-2010 may be substantially similar or identical to blocks 1000-1006, respectively, as described above with regard to FIG. 1.

Figure 4:
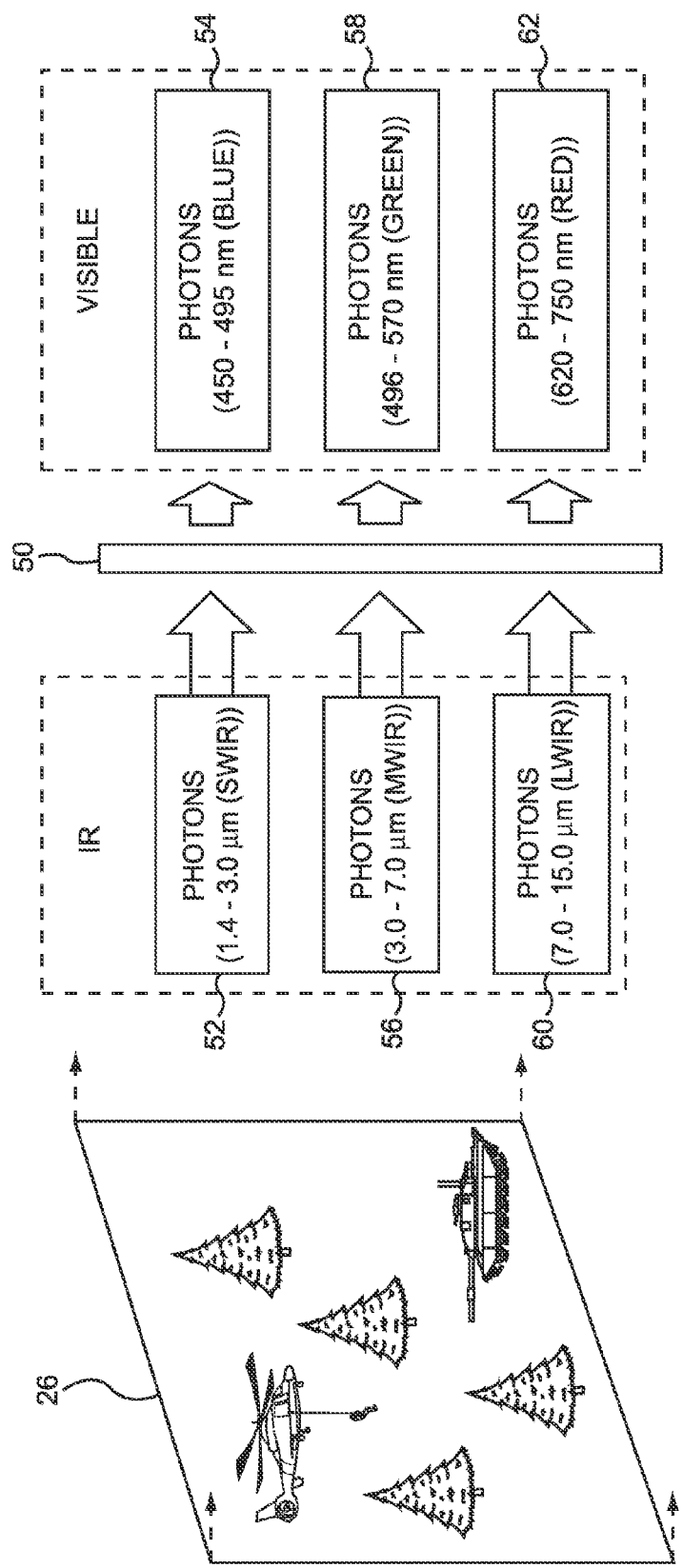
FIG. 4 is a block diagram illustrating an example conversion of pluralities of photons in received bands to corresponding pluralities of photons in converted bands according to one embodiment.

FIG. 4 is a block diagram illustrating an example conversion of pluralities of photons in received bands to corresponding pluralities of photons in converted bands according to one embodiment. In this embodiment, a NP photon conversion material 50 is configured to convert a plurality of photons 52 in a short-wave infrared band comprising wavelengths of about 1.4 μm to about 3.0 μm to a plurality of photons 54 in a blue visible band comprising wavelengths of about 450 nm to about 495 nm. The NP photon conversion material 50 is also configured to convert a plurality of photons 56 in a mid-wave infrared band comprising wavelengths of about 3.0 μm to about 7.0 μm to a plurality of photons 58 in a green visible band comprising wavelengths of about 496 nm to about 570 nm. The NP photon conversion material 50 is also configured to convert a plurality of photons 60 in a long-wave infrared band comprising wavelengths of about 7.0 μm to about 15.0 μm to a plurality of photons 62 in a red visible band comprising wavelengths of about 620 nm to about 750 nm.

Figure 5:
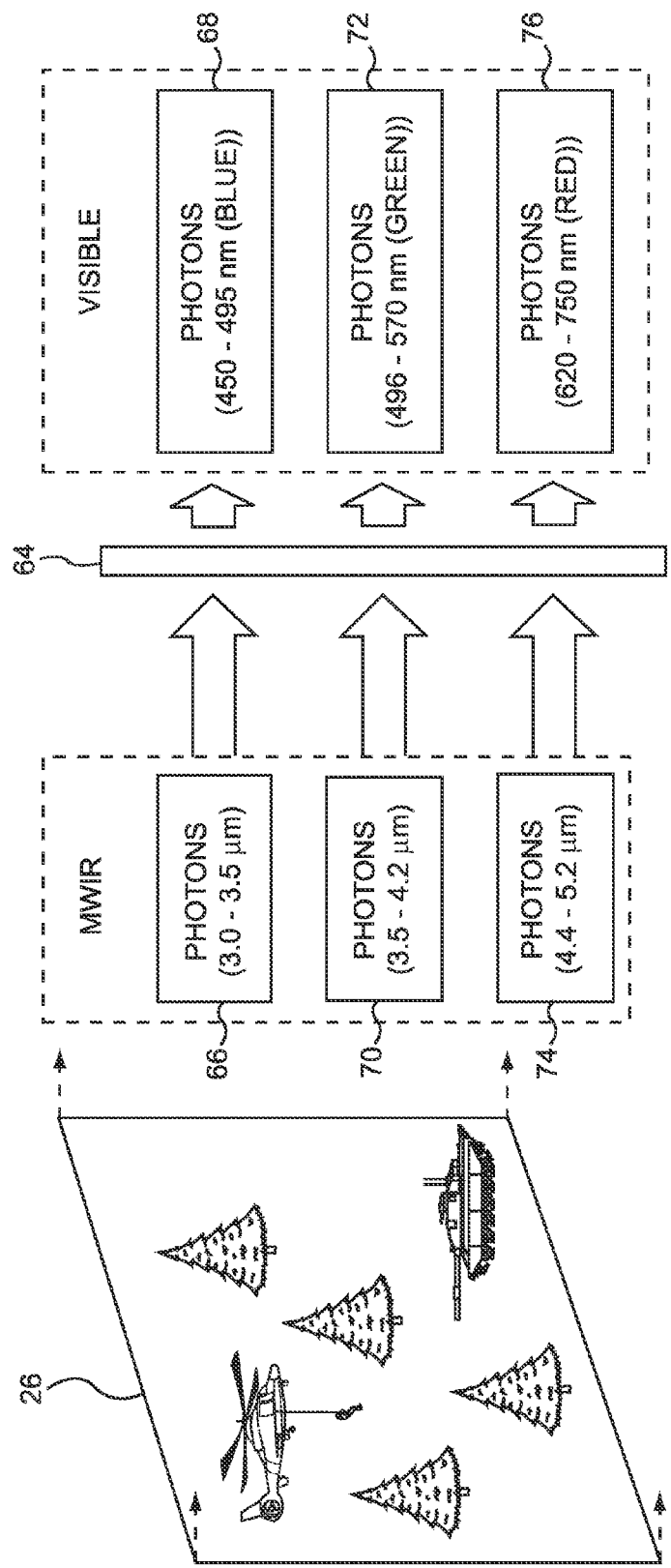
FIG. 5 is a block diagram illustrating an example conversion of pluralities of photons in received bands to corresponding pluralities of photons in converted bands according to another embodiment.

FIG. 5 is a block diagram illustrating an example conversion of pluralities of photons in received bands to corresponding pluralities of photons in converted bands according to another embodiment. In this embodiment, a NP photon conversion material 64 is configured to convert a plurality of photons 66 in a first mid-wave infrared band comprising wavelengths of about 3.0 μm to about 3.5 μm to a plurality of photons 68 in a blue visible band comprising wavelengths of about 450 nm to about 495 nm. The NP photon conversion material 64 is also configured to convert a plurality of photons 70 in a second mid-wave infrared band comprising wavelengths of about 3.5 μm to about 4.2 μm to a plurality of photons 72 in a green visible band comprising wavelengths of about 496 nm to about 570 nm. The NP photon conversion material 64 is also configured to convert a plurality of photons 74 in a third mid-wave infrared band comprising wavelengths of about 4.4 μm to about 5.2 μm to a plurality of photons 76 in a red visible band comprising wavelengths of about 620 nm to about 750 nm. Thus, as illustrated by FIGS. 4 and 5, any desired granularity of photons of received bands may be converted to a corresponding converted band for imaging by the image sensor 28.

Figure 6:
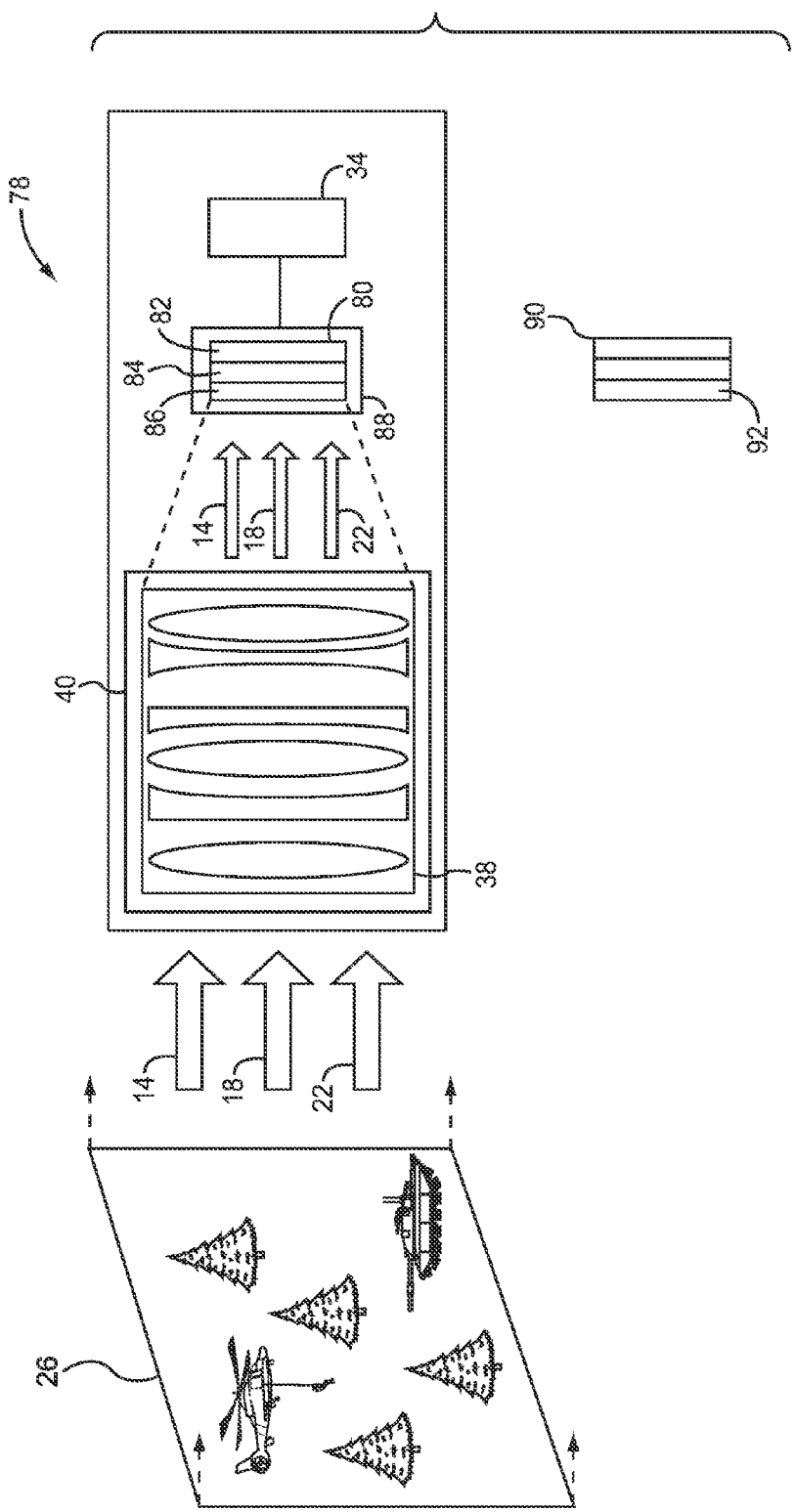
FIG. 6 illustrates a block diagram of a multi-spectral imaging apparatus according to another embodiment.

While FIGS. 5 and 6, for purposes of illustration, discuss the conversion of photons in infrared received bands, the embodiments are not so limited. The embodiments have applicability in a variety of received bands, including the X-ray and ultraviolet received bands.

FIG. 6 illustrates a block diagram of an imaging apparatus 78 according to another embodiment. In this embodiment, the imaging apparatus 78 comprises an image sensor 80 that comprises readout circuitry 82, photodetector array 84, and a NP photon conversion material 86. Thus, in this embodiment, the NP photon conversion material 86 is integrated with the photodetector array 84 and the readout circuitry 82. In this embodiment, a manufacturer of the image sensor 80 may apply the NP photon conversion material 86 onto a surface that is in proximity to the photodetector array 84, such as one or more microns from the photodetector array 84.

In this embodiment, the NP photon conversion material 86 may be configured to convert pluralities of photons 14, 18, 22 of particular received bands into corresponding pluralities of photons of converted bands, but be ineffective at converting photons of other received bands. Accordingly, the imaging apparatus 78 may include an image sensor receiver 88 that has a released mode and an engaged mode, and is configured to fix the image sensor 80 with respect to the lens arrangement 38 when in the engaged mode. In order to detect different pluralities of received bands, the user may release the image sensor 80 from the image sensor receiver 88, and insert a suitable second image sensor 90 into the image sensor receiver 88. The second image sensor 90 may include a second NP photon conversion material 92 that is configured to convert different pluralities of received bands to corresponding pluralities of photons of converted bands than that of the NP photon conversion material 86.

Figure 7:
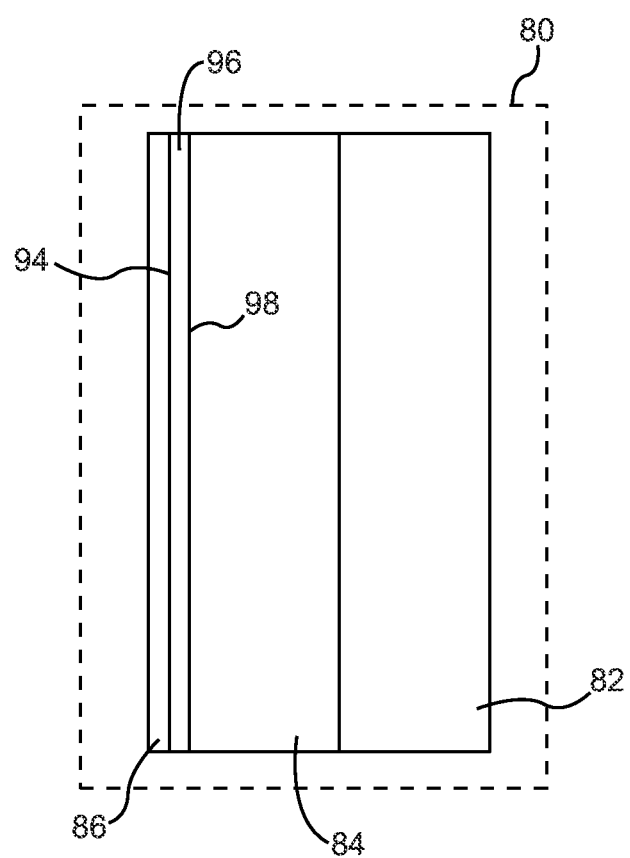
FIG. 7 is a block diagram of an image sensor illustrated in FIG. 6 according to one embodiment.

FIG. 7 is a block diagram of the image sensor 80 according to one embodiment. The NP photon conversion material 86 may be coated on a first surface 94 of a glass, or other transmissive substrate 96. The substrate 96 may comprise any suitable transmissive substrate that allows the emission of photons in converted bands toward the photodetector array 84. A second surface 98 of the substrate 96 is adjacent to the photodetector array 84. In one embodiment, the NP photon conversion material 86 coated on the first surface 94 of the transmissive substrate 96 is a distance no more than one order (<10) of the converted band of wavelengths away from the photodetector array 84.

The present embodiments, for purposes of illustration, have been described in the context of particular received bands and particular converted bands, but the embodiments are not so limited, and apply to any received bands that may be converted to any converted bands by a suitable NP photon conversion material. Other non-limiting examples of such bands include a first received band that comprises a long-wave infrared band, a second received band that comprises a first mid-wave infrared band, a first converted band that comprises a second mid-wave infrared band that is different from the first mid-wave infrared band, and a second converted band that comprises a short-wave infrared band. Additional non-limiting examples include the conversion of one or more received long-wave infrared bands to one or more corresponding converted short-wave infrared bands, the conversion of one or more received ultraviolet bands to one or more corresponding converted visible (e.g., red, blue, or green) bands, and the conversion of one or more received X-ray bands to one or more corresponding converted ultraviolet bands.

The present embodiments have wide applicability and may be utilized in any context in which the detection and imaging of electromagnetic radiation is desirable. One example application includes, for example, the conversion of pluralities of photons in mid-wave infrared received bands to corresponding pluralities of photons in converted bands for use in target recognition applications based on shape and spectral content. Another application includes, for example, the conversion of pluralities of photons in ultraviolet received bands in conjunction with the conversion of pluralities of photons in a mid-wave infrared received band to corresponding pluralities of photons in converted bands for use in missile warning systems. Such application may facilitate hot plume detection with significant clutter reduction. Additional applications include the conversion of pluralities of ultraviolet received bands to corresponding converted bands in fingerprint applications, factory quality imaging applications, various consumer products, and hot plume imaging. The embodiments also have applicability in realtime X-ray applications, such as medical applications, security applications, manufacturing applications, applications in the food industry, and the like. The embodiments also have wide applicability in spectroscopy applications.

Figure 8:
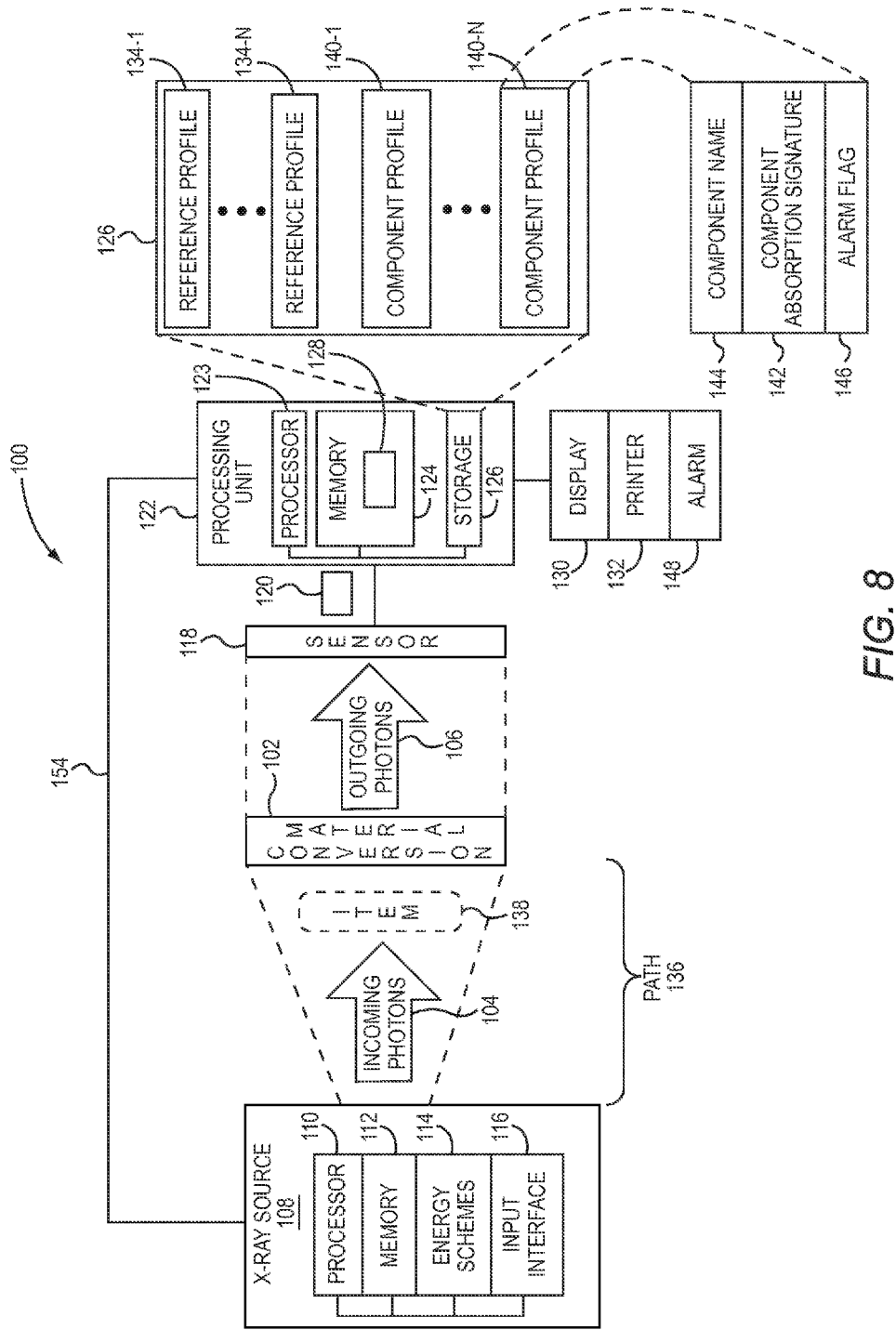
FIG. 8 is a block diagram of a system in which additional embodiments may be practiced.

FIG. 8 is a block diagram of a system 100 in which additional embodiments may be practiced. The system 100 includes a conversion material 102 that is configured to convert one or more pluralities of photons in received bands to corresponding pluralities of photons in converted bands. The conversion material 102 may be similar or identical to the first NP photon conversion material 12 discussed above with regard to FIGS. 1-7. In these embodiments, the conversion material 102 converts incoming photons 104 in X-ray bands to outgoing photons 106 in converted bands that are in, for example, the visible-to-near infrared (VNIR) spectrum, such as photons having wavelengths between about 400 nm to about 1,400 nm. The phrases "incoming" and "outgoing," such as the incoming photons 104 and outgoing photons 106, as used herein, are with respect to the conversion material 102.

The system 100 also includes an X-ray source 108 that is configured to emit the incoming photons 104 toward the conversion material 102. The incoming photons 104 comprise photons in multiple bands of the X-ray spectrum. The X-ray source 108 may include a processor 110 and a memory 112. In one embodiment, the X-ray source 108 may be configured to emit the incoming photons 104 in accordance with a particular energy scheme 114. Each particular energy scheme 114 may identify a plurality of different X-ray bands, and different output, power, or intensity levels associated with each different X-ray band.

The X-ray source 108 may include an input interface 116 to facilitate the entry, by an operator, of a particular energy scheme 114. Upon receipt of the selection of the particular energy scheme 114, the X-ray source 108 emits the incoming photons 104 in accordance with the particular energy scheme 114.

The X-ray source 108 may comprise any suitable broadband X-ray generator, including, by way of non-limiting example, a rotating anode tube, a Crookes tube, a Coolidge tube, and a microfocus X-ray tube, and the like.

A sensor 118 receives the outgoing photons 106. The sensor 118 may include a photodetector array and readout circuitry (not illustrated). The sensor 118 generates output data 120 that is representative of the outgoing photons 106. A processing unit 122 is coupled to the sensor 118 and receives the output data 120. The processing unit 122 may include a processor 123, a memory 124, and a storage 126. The processing unit 122 generates image data 128 based on the output data 120. In some embodiments, the processing unit 122 may communicate the image data 128 to a display 130 for presentation to an operator, and/or provide the image data to a printer 132 for printing.

During a setup, or calibration, phase of the system 100, one or more reference profiles 134-1-134-N (generally, reference profiles 134) may be determined. Each reference profile 134 identifies a pattern of the outgoing photons 106 emitted by the conversion material 102 when the conversion material 102 receives the incoming photons 104 without anything in a path 136 between the X-ray source 108 and the conversion material 102. Each reference profile 134 may be associated with a corresponding energy scheme 114. Thus, when the X-ray source 108 emits the incoming photons 104 in accordance with a particular energy scheme 114, the corresponding reference profile 134 identifies the pattern of outgoing photons 106 emitted by the conversion material 102. The pattern may be quantified in any desirable manner, such as, for example, a spectral and intensity distribution of the energy in each band of the plurality of converted bands emitted by the conversion material 102 when the conversion material 102 receives incoming photons 104 generated in accordance with the particular energy scheme 114.

During operation of the system 100, an item 138 may be positioned in the path 136 from the X-ray source 108 to the conversion material 102. The item 138 may be a living item, such as a human or other animal, or may be a manufactured item, for example. Typically the item 138 will absorb some of the incoming photons 104 in one or more of the X-ray bands. In one embodiment, the processing unit 122 may determine an absorption signature of the item 138 based on the output data 120 and the respective reference profile 134 associated with the particular energy scheme 114 used by the X-ray source 108 to emit the incoming photons 104.

The processing unit 122 may compare the absorption signature of the item 138 to one or more component profiles 140-1-140-N (generally, component profiles 140). Each component profile 140 corresponds to a particular component of the item 138. A component may comprise a chemical element, such as oxygen, carbon, tin, or the like, or a mixture of chemical elements, or a molecule, or any other substance which can be identified based on its absorption of X-ray energy. Each component profile 140 includes a component absorption signature 142 that identifies the absorption characteristics of the corresponding component. A component profile 140 may also include a component name 144 that contains an identifier of the component. The component profile 140 may also include an alarm flag 146, which, if set to TRUE, may be utilized by the processing unit 122 to initiate an alarm 148 that is perceivable by an operator.

It should be noted that in some embodiments the system 100 may include optics for focusing the incoming photons 104 on the conversion material 102, or for focusing the outgoing photons 106 on the sensor 118.

Figure 9:
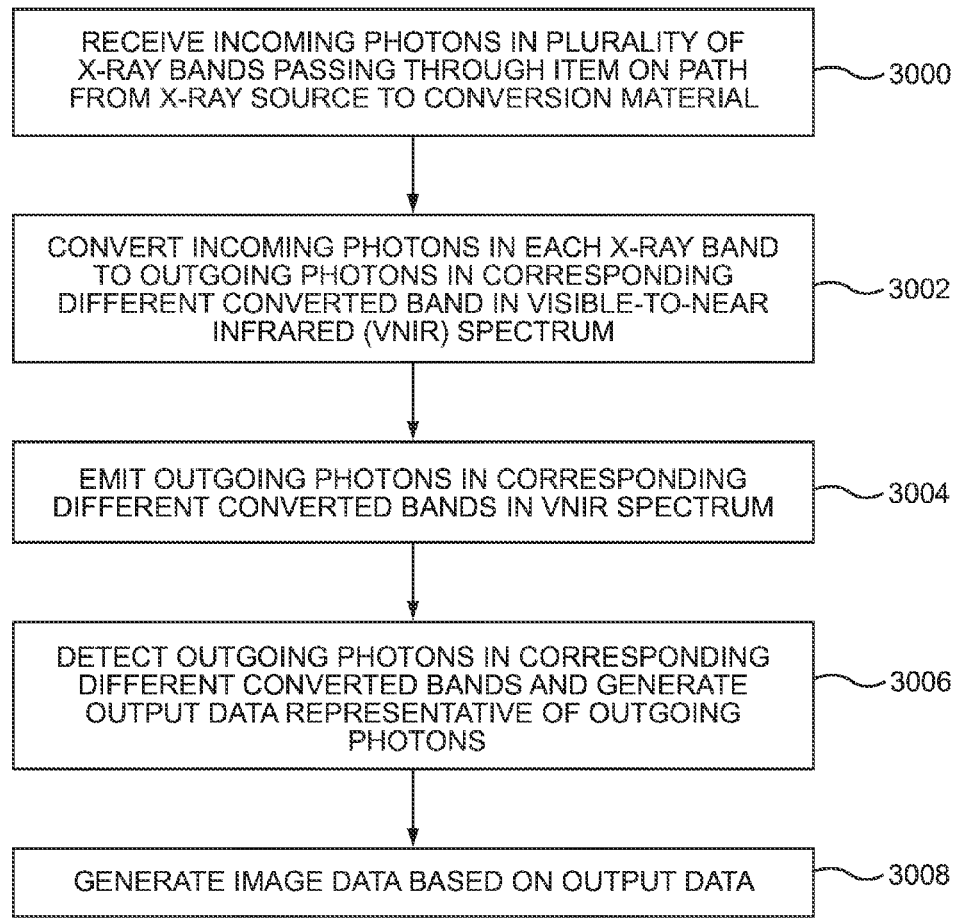
FIG. 9 is a flowchart for generating an image according to one embodiment.

FIG. 9 is a flowchart for generating an image according to one embodiment, and will be discussed in conjunction with FIG. 8. Assume, for purposes of illustration, that the item 138 is a dog, and an operator sets the X-ray source 108 to emit the incoming photons 104 in accordance with an energy scheme 114 that emits incoming photons 104 in multiple different X-ray bands, the particular wavelengths of which may be absorbed by certain cancers. The X-ray source 108 emits the incoming photons 104 in accordance with the selected energy scheme 114. The conversion material 102 receives the incoming photons 104 in the plurality of X-ray bands that pass through the dog in the path 136 from the X-ray source 108 to the conversion material 102 (FIG. 8, block 3000). The conversion material 102 converts the incoming photons 104 in each X-ray band to a corresponding different converted band in the VNIR spectrum (FIG. 8, block 3002). The conversion material 102 emits the outgoing photons 106 in the corresponding different converted bands (FIG. 8, block 3004). While the conversion and emission of photons are described as sequential steps for purposes of illustration, such steps may occur substantially simultaneously.

The sensor 118 detects the outgoing photons 106 in the corresponding different converted bands and generates output data 120 that is representative of the outgoing photons 106 (FIG. 8, block 3006). The processing unit 122 generates the image data 128 based on the output data 120 (FIG. 8, block 3008). In particular, the processing unit 122 may utilize the reference profile 134 that corresponds to the selected energy scheme 114 to determine differences between the reference profile 134 and the outgoing photons 106. Such differences reflect energy that has been absorbed by the dog as the incoming photons 104 passed through the dog. The processing unit 122 may, for each X-ray band in which absorption has occurred, depict such band with a different visible color. The processing unit 122 may also determine an absorption signature based on the output data 120, and compare the absorption signature to one or more component profiles 140. The processing unit 122 may find a match of the absorption signature with a particular component profile 140, extract the component name 144 from the component profile 140, and display the component name 144 to the operator on the display 130.

Figure 10:
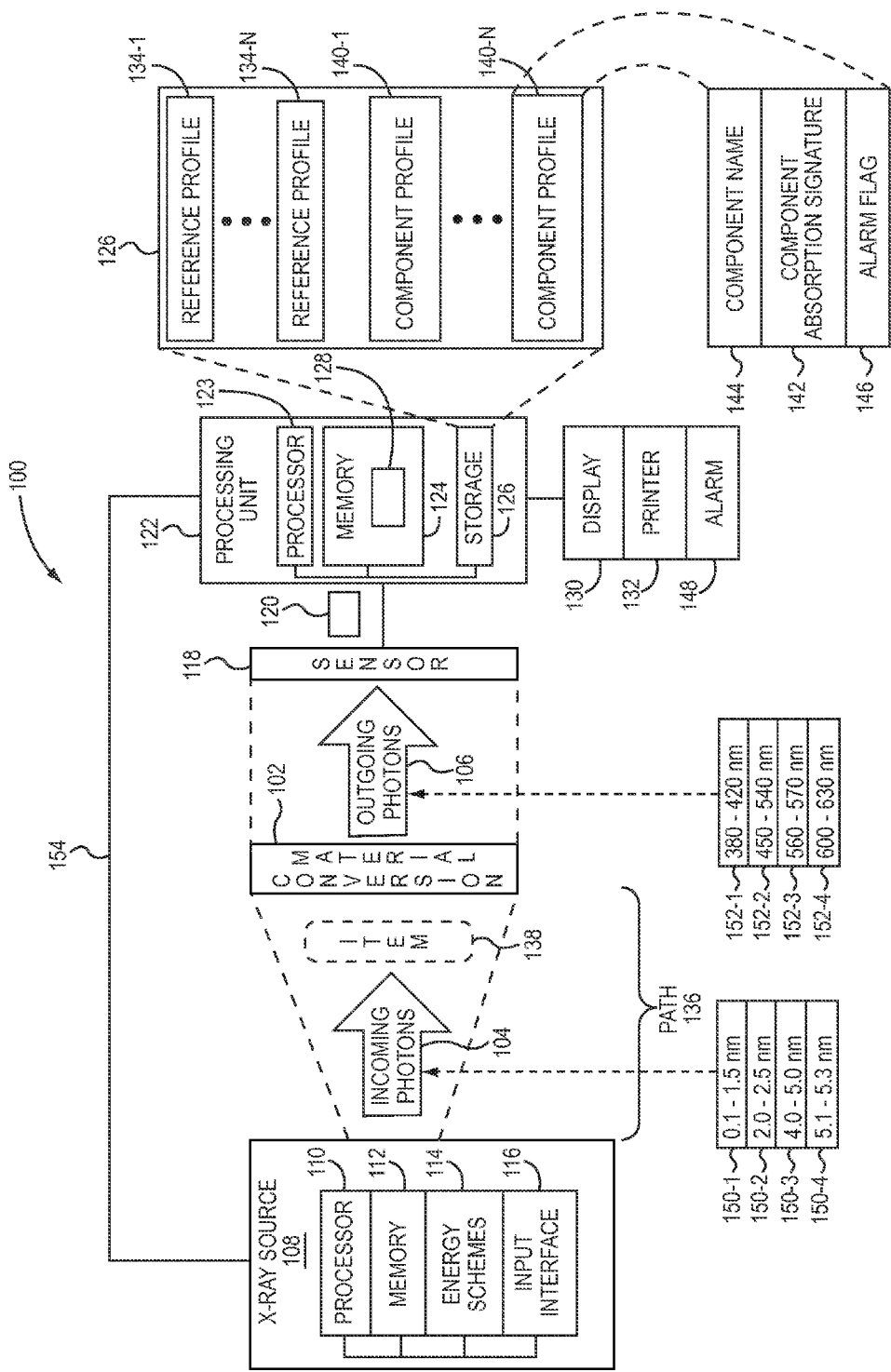
FIG. 10 is a block diagram of the system illustrated in FIG. 8 wherein a particular energy scheme has been selected.

FIG. 10 is a block diagram of the system illustrated in FIG. 8 wherein a particular energy scheme 114 has been selected. In this example, the incoming photons 104 comprise photons in four X-ray bands 150-1-150-4 (generally, X-ray bands 150). Specifically, the X-ray band 150-1 comprises photons having a wavelength of 0.1-1.5 nanometers (nm); the X-ray band 150-2 comprises photons having a wavelength of 2.0-2.5 nm; the X-ray band 150-3 comprises photons having a wavelength of 4.0-5.0 nm; and the X-ray band 150-4 comprises photons having a wavelength of 5.1-5.3 nm. The conversion material 102 has been designed to convert the X-ray bands 150-1-150-4 to corresponding different converted bands 152-1-152-4 (generally, converted bands 152) in the VNIR spectrum. Specifically, the conversion material 102 converts the incoming photons 104 in the X-ray band 150-1 to outgoing photons 106 in the converted band 152-1 having a wavelength of 380-420 nm; the conversion material 102 converts the incoming photons 104 in the X-ray band 150-2 to outgoing photons 106 in the converted band 152-2 having a wavelength of 450-540 nm; the conversion material 102 converts the incoming photons 104 in the X-ray band 150-3 to outgoing photons 106 in the converted band 152-3 having a wavelength of 560-570 nm; and the conversion material 102 converts the incoming photons 104 in the X-ray band 150-4 to outgoing photons 106 in the converted band 152-4 having a wavelength of 600-630 nm.

Note that the example wavelengths of the X-ray bands 150 and the converted bands 152 are simply examples, and the conversion material 102 may convert incoming photons 104 of any desired band of wavelengths in the X-ray spectrum to corresponding outgoing photons 106 in any desired band of wavelengths in the VNIR spectrum.

In one embodiment, the X-ray source 108 is communicatively coupled to the processing unit 122 via a communications link 154. The communications link 154 can comprise any suitable wired or wireless technology, or combination of technologies, including one or more networks, capable of facilitating communications between the X-ray source 108 and the processing unit 122. In one embodiment, as an operator selects a particular energy scheme 114 via the input interface 116, the X-ray source 108 communicates an energy scheme identifier that identifies the particular energy scheme 114 to the processing unit 122. The processing unit 122 may use the energy scheme identifier to select the corresponding reference profile 134 that identifies the pattern of the outgoing photons 106 emitted by the conversion material 102 when the conversion material 102 receives the incoming photons 104 emitted in accordance with the particular energy scheme 114, without anything in the path 136 between the X-ray source 108 and the conversion material 102.

As discussed above, in a security context, one or more of the component profiles 140 may have the alarm flag 146 set to TRUE. When used in such security context, the item 138 may comprise, for example, luggage, boxes, crates at customs locations, and any other article that may be made of, or may surround, a component that is deemed hazardous, or otherwise alarm-worthy. The item 138 may be irradiated with the incoming photons 104 in accordance with a particular energy scheme 114, and the processing unit 122 may utilize the corresponding reference profile 134 to determine an absorption signature of the item 138. The processing unit 122 may compare the absorption signature of the item 138 to each component absorption signature 142 of each component profile 140. If a match is determined, and the alarm flag 146 of the component profile 140 contains the matched component absorption signature 142, the processing unit 122 may initiate the alarm 148. In some embodiments, the processing unit 122 may use the component name 144 to identify for the operator the particular component that matched the absorption signature of the item 138. If no match is found, the processing device 122 may also indicate that no match has been found on the display 130, for example. The operator may select another energy scheme 114, and the process may be repeated, or the item 138 may be deemed not to be alarm-worthy.

In the context of medicine, the item 138 may comprise a human or other animal. In accordance with embodiments disclosed herein, the item 138 may be irradiated with multiple different bands of X-ray energy simultaneously. Based on the absorption signature of the item 138, the makeup of undesired masses in the item 138, such as cysts, cancers, or tumors, may be identified by the processing unit 122. In a related application, the embodiments have applicability in X-ray computer tomography using spectral imaging techniques to further refine and improve on resolution through wavelength diversity processing.

In the context of manufacturing, the item 138 may comprise a manufactured item. The item 138 may receive incoming photons 104 in accordance with an energy scheme 114 that may result in certain absorption signals that reflect an improper weld, seam, or other defect in the manufacturing process. The embodiments also have applicability in X-ray crystallography, wherein various relatively narrow bands may enable simultaneous X-ray multiband crystallography in order to provide multiple solutions to the diffraction.

In yet another application, the embodiments have applicability in X-ray astronomy, to differentiate between types of celestial bodies and events.

The embodiments also have applicability in the context of scanning electron microscopy.

FIG. 11 is a block diagram of the sensor 118 according to another embodiment. In this embodiment, the conversion material 102 may be placed on, or inserted into, a scanner bed 156. The sensor 118 comprises a plurality of rows 158 of photodetector elements. Each row 158 of photodetector elements may be configured to detect outgoing photons 106 of a particular converted band. For example, each row 158 of photodetector elements may comprise a filter tuned to pass outgoing photons 106 of a particular band. In the example shown in FIG. 11, the sensor 118 comprises seven rows 158 of photodetector elements, and thus is configured to detect seven different converted bands of outgoing photons 106. In other embodiments, the sensor 118 may comprise any number of rows 158 of photodetector elements necessary for detecting the desired number of different converted bands of outgoing photons 106. In operation, the sensor 118 may travel along guides 160 across the conversion material 102 at a rate that allows the rows 158 of photodetector elements to detect the outgoing photons 106 and continuously provide output data 120 to the processing unit 122 as each row 158 is incrementally displaced along the guides 160.

Those skilled in the art will recognize improvements and modifications to the preferred embodiments of the present disclosure. All such improvements and modifications are considered within the scope of the concepts disclosed herein and the claims that follow.

What is claimed is:

1. A method of generating image data, comprising:
    receiving, by a nanoparticle photonic conversion layer, incoming photons in a plurality of X-ray bands, the incoming photons passing through an item on a path from an X-ray source to the nanoparticle photonic conversion layer;
    converting the incoming photons in each X-ray band of the plurality of X-ray bands to outgoing photons in corresponding different converted bands in the visible-to-near infrared (VNIR) spectrum;
    emitting, by the nanoparticle photonic conversion layer, the outgoing photons in the corresponding different converted bands in the VNIR spectrum;
    detecting, by a sensor, the outgoing photons in the corresponding different converted bands in the VNIR spectrum and generating output data representative of the outgoing photons; and
    generating image data based on the output data.

2. The method of claim 1, further comprising:
    receiving a selection of a particular energy scheme of a plurality of energy schemes; and
    based on the selection, emitting the incoming photons in the plurality of X-ray bands in accordance with the particular energy scheme.

3. The method of claim 1, wherein the incoming photons are emitted by the X-ray source in a known pattern that is identified in a reference profile; and
    wherein generating the image data based on the output data comprises generating the image data based on the output data and the reference profile.

4. The method of claim 3, further comprising:
    receiving, by a processor, an energy scheme identifier; and
    based on the energy scheme identifier, accessing the reference profile from a plurality of reference profiles.

5. The method of claim 3, wherein the reference profile identifies a spectral distribution and intensity emitted by the nanoparticle photonic conversion layer upon receiving incoming photons transmitted by the X-ray source without any item in the path between the X-ray source and the nanoparticle photonic conversion layer.

6. The method of claim 1, further comprising:
    determining an absorption signature of the item based on the output data; and
    based on the absorption signature, identifying a component of the item.

7. The method of claim 6, wherein identifying the component of the item comprises:
    comparing the absorption signature of the item to one or more component profiles, each component profile identifying a different respective absorption signature associated with a respective component.

8. The method of claim 7, wherein the absorption signature of the item matches a component profile of a material identified as hazardous, and further comprising initiating an alarm.

9. The method of claim 7, wherein the item is a manufactured item, and wherein the absorption signature identifies a defect in the manufactured item.

10. The method of claim 1, wherein the plurality of X-ray bands comprises at least four X-ray bands.

11. A system, comprising:
    a nanoparticle photonic conversion layer configured to:
        receive incoming photons in a plurality of X-ray bands, the incoming photons passing through an item on a path from an X-ray source to the nanoparticle photonic conversion layer;
        convert the incoming photons in each X-ray band of the plurality of X-ray bands to outgoing photons in corresponding different converted bands in the visible-to-near infrared (VNIR) spectrum; and
        emit the outgoing photons in the corresponding different converted bands in the VNIR spectrum;
    at least one sensor configured to detect the outgoing photons in the corresponding different converted bands in the VNIR spectrum and generating output data representative of the outgoing photons; and
    a processing unit configured to generate image data based on the output data.

12. The system of claim 11, further comprising the X-ray source.

13. The system of claim 12, wherein the X-ray source is configured to:
    receive a selection of a particular energy scheme of a plurality of energy schemes; and
    based on the selection, emit the incoming photons in the plurality of X-ray bands in accordance with the particular energy scheme.

14. The system of claim 12, wherein the X-ray source is configured to emit the incoming photons in a known pattern that is identified in a reference profile; and
    wherein to generate the image data based on the output data, the processing unit is further configured to generate the image data based on the output data and the reference profile.

15. The system of claim 14, wherein the processing unit is further configured to:
    receive an energy scheme identifier; and
    based on the energy scheme identifier, access the reference profile from a plurality of reference profiles.

16. The system of claim 14, wherein the reference profile identifies a spectral distribution and intensity emitted by the nanoparticle photonic conversion layer upon receiving incoming photons transmitted by the X-ray source without any item in the path between the X-ray source and the nanoparticle photonic conversion layer.

17. The system of claim 11, wherein the processing unit is further configured to:
    determine an absorption signature of the item based on the output data; and
    based on the absorption signature, identify a component of the item.

18. The system of claim 17, wherein to identify the component of the item the processing unit is further configured to:
    compare the absorption signature of the item to one or more component profiles, each component profile identifying a different respective absorption signature associated with a respective component.

19. The system of claim 18, wherein the processing unit is further configured to:
   make a determination that the absorption signature of the item matches a component profile of a material identified as hazardous; and
   based on the determination, initiate an alarm.

20. The system of claim 18, wherein the item is a manufactured item, and wherein the absorption signature identifies a defect in the manufactured item.

21. The system of claim 11, wherein the plurality of X-ray bands comprises at least four X-ray bands.

* * * * *

UNITED STATES PATENT AND TRADEMARK OFFICE
CERTIFICATE OF CORRECTION

PATENT NO. : 9,478,692 B1
APPLICATION NO. : 14/095513
DATED : October 25, 2016
INVENTOR(S) : David R. Twede et al.

Page 1 of 1

It is certified that error appears in the above-identified patent and that said Letters Patent is hereby corrected as shown below:

On the Title Page

Item (73), Replace:
"Assignee: Lackheed Martin Corporation, Bethesda, MD (US)"
With:
--"Assignee: Lockheed Martin Corporation, Bethesda, MD (US)"--.

Signed and Sealed this
Twenty-sixth Day of November, 2019

Andrei Iancu
*Director of the United States Patent and Trademark Office*